United States Patent [19]

Pawelchak et al.

[11] 4,292,972

[45] Oct. 6, 1981

[54] LYOPHILIZED HYDROCOLLOIO FOAM

[75] Inventors: John M. Pawelchak, Belle Mead; Yu-Chang J. Wang, North Brunswick; Anthony L. LaVia, East Brunswick, all of N.J.

[73] Assignee: E. R. Squibb & Sons, Inc., Princeton, N.J.

[21] Appl. No.: 167,257

[22] Filed: Jul. 9, 1980

[51] Int. Cl.$^3$ ............................................. A61F 13/00
[52] U.S. Cl. ................................. 128/296; 128/156; 128/334 R; 260/117; 264/50; 424/28
[58] Field of Search ................................. 128/155–156, 128/296, 334 R; 424/28, 34, 35, 37, 360, 361; 264/50, 348; 260/117

[56] References Cited

U.S. PATENT DOCUMENTS

| | | |
|---|---|---|
| 2,423,475 | 7/1947 | Bice et al. |
| 2,465,357 | 3/1949 | Correll |
| 2,507,244 | 5/1950 | Correll |
| 2,558,395 | 6/1951 | Studer |
| 2,597,011 | 5/1952 | McMasters et al. |
| 2,602,042 | 7/1952 | Abbott |
| 2,712,672 | 7/1955 | Calcagno |
| 2,764,159 | 9/1956 | Masci et al. |
| 2,772,999 | 12/1956 | Masci et al. |
| 2,773,000 | 12/1956 | Masci et al. |
| 2,824,092 | 2/1958 | Thompson |
| 2,899,362 | 8/1959 | Sieger, Jr. et al. |
| 2,923,664 | 2/1960 | Cook et al. |
| 3,005,457 | 10/1961 | Millman et al. |
| 3,122,479 | 2/1964 | Smith |
| 3,157,524 | 11/1964 | Artandi |
| 3,312,594 | 4/1967 | Cyr et al. |
| 3,325,366 | 6/1967 | Blaug et al. |
| 3,328,259 | 6/1967 | Anderson |
| 3,339,546 | 9/1967 | Chen |
| 3,368,911 | 8/1967 | Kuntz et al. |
| 3,438,374 | 4/1969 | Falb et al. |
| 3,471,598 | 10/1969 | Battista |
| 3,632,361 | 1/1972 | Battista |
| 3,640,741 | 2/1972 | Etes |
| 3,653,383 | 4/1972 | Wise |
| 3,767,784 | 10/1973 | Gluck |
| 3,810,473 | 5/1974 | Cruz, Jr. et al. |
| 3,813,466 | 5/1974 | Anderson |
| 3,939,831 | 2/1976 | Cioca et al. |
| 4,002,173 | 1/1977 | Manning et al. |
| 4,191,751 | 3/1980 | Gottlieb |

FOREIGN PATENT DOCUMENTS 900868 7/1962 United Kingdom .

OTHER PUBLICATIONS

Johnson Johnson, Surgical, Bulletin.
Morgenstern et al., *Arch Surgery*, vol. 112, Aug. 77, pp. 941–943.
Avitene, Medical Dept. Avicon, Inc., Ft. Worth, TX.
Matsumoto, Chem. Abst. vol. 82, 7641m.
Oleneva et al., Chem. Abst. vol. 76, 26624a.
Barth et al., Chem. Abst. vol. 02, 4679i.
Lowry, *Arch of Surg.* vol. 60, pp. 793–805.
Lachman et al. *Jour. of Amer. Phar. Assoc.*, vol. 46, pp. 412–416.
Pereiras et al., *Radiology*, vol. 24, pp. 313–322.
Hama, Chem. Abst., vol. 81, 3495g.
Hanudelova, Chem. Abst. vol. 81, 68597c.
Sako et al., Chem. Abst., vol. 75, 101307j.

*Primary Examiner*—C. Fred Rosenbaum
*Attorney, Agent, or Firm*—Lawrence S. Levinson; Stephen B. Davis

[57] ABSTRACT

A lyophilized foam sponge product having medically useful hemostatic and adhesive properties formed from the hydrocolloids, gelatin, pectin, and sodium carboxymethylcellulose and having a density of from about 0.01 to about 0.10 grams/cc. The gelatin is present at from about 20% to about 80% by weight of the final product and the pectin and sodium carboxymethylcellulose are each present at from about 10% to about 50% by weight of the final product. The product is prepared by forming an aqueous colloidal dispersion of hydrocolloids, aerating or foaming, freezing, and lyophilizing.

30 Claims, No Drawings

LYOPHILIZED HYDROCOLLOID FOAM

BACKGROUND OF THE INVENTION

Various types of hemostatic sponges and powders have been proposed. For example, Correll in U.S. Pat. No. 2,465,357 discloses a cross-linked gelatin sponge and in U.S. Pat. No. 2,507,244, discloses a cross-linked gelatin powder. Studer in U.S. Pat. No. 2,558,395 discloses a hemostatic sponge prepared by freeze drying a foam of an aqueous solution of gelatin and thrombin. Calcagno in U.S. Pat. No. 2,712,672 discloses a gelatin sponge prepared by treating the frozen mass with a dehydrating liquid. Other freeze dried gelatin hemostatic products are disclosed by Hama et al., Chem. Abst. Vol. 47, 3495 g, Sako et al., Chem. Abst. Vol. 75, 101307 j and Hanudelova et al., Chem. Abstr., Vol. 81, 68597c.

Smith in U.S. Pat. No. 3,122,479 discloses the hemostatic properties of oxidized cellulose such as carboxymethyl cellulose in the form of a film, sponge, dried foam, or freeze dried sponge. Millman et al. in U.S. Pat. No. 3,005,457 discloses a hemostatic methyl cellulose sponge. Masci et al. in U.S. Pat. No. 2,764,159 discloses a freeze dried hemostatic sponge of cellulose glycolic acid ether in free acid form, i.e., carboxymethyl cellulose. Cook et al. in U.S. Pat. No. 2,923,664 disclose a hemostatic tablet formed by the wet granulation and compression of a mixture of cellulose glycolic acid ether and its sodium salt. Masci et al. in U.S. Pat. Nos. 2,772,999 and 2,773,000 disclose impregnating carboxymethyl cellulose in the free acid or salt form onto the surface of a gauze dressing to act as a hemostatic agent.

Abbott in U.S. Pat. No. 2,602,042 describes the use of methyl cellulose as a wound dressing or in powder form for direct application to burns or wounds. Anderson in U.S. Pat. Nos. 3,328,250 and 3,813,466 describes the hemostatic properties of sodium carboxymethyl cellulose.

Battista in U.S. Pat. Nos. 3,471,598 and 3,632,361 discloses an absorbent mat or sponge like material formed by freeze drying an aqueous dispersion of microcrystalline collagen. Cruz et al. in U.S. Pat. No. 3,810,473 disclose a hemostat-adhesive material in a fluffy, finely divided fibrous form consisting of vacuum dried or freeze dried water-insoluble, ionizable collagen.

Kuntz et al. in U.S. Pat. No. 3,368,911 disclose a hemostatic sponge prepared by freeze drying acid swollen collagen fibrils. Freeze dried collagen dressings are disclosed by Cioca et al. in U.S. Pat. No. 3,939,831 and Matsumoto et al. in Chem. Abst. Vol. 82, 7461 m. Artandi in U.S. Pat. No. 3,157,524 discloses collagen sponges prepared in a different manner.

Manning et al. in U.S. Pat. No. 4,022,173 disclose hemostatic sponges prepared by freeze drying water soluble salts of amylose succinate or amylose glutarate followed by a crosslinking step. Rutenberg et al. in British Patent No. 900,868 are directed to preparing amylose sponges by forming an aqueous dispersion of the amylose, foaming the dispersion by heating or bubbling an inert gas, and then permitting the foam to set to the insoluble state caused by the retrogradation of the amylose. Wise in U.S. Pat. No. 3,653,383 describes a surgical sponge prepared by freeze drying an aqueous algin dispersion or gel. Surgical sponges prepared from starch material are disclosed by Bice et al. in U.S. Pat. No. 2,423,475 and Mac Masters et al. in U.S. Pat. No. 2,597,011. Freeze dried starch sponges are disclosed by Oleneva et al., Chem. Abst. Vol. 76,26624 a.

Blaug et al. in U.S. Pat. No. 3,325,366 disclose an hemostatic foam prepared from an aqueous solution of gelatin and polyvinylpyrrolidone. Sieger et al. in U.S. Pat. No. 2,899,362 disclose a hemostatic sponge made from a solution of gelatin and starch. Gluck in U.S. Pat. No. 3,767,784 describes an aerated foam or solid wound healing composition including gelatin and a carbohydrate. Thompson in U.S. Pat. No. 2,824,092 describes freeze drying an aqueous mixture of gelatin and carboxymethylcellulose to prepare a pharmaceutically useful product.

Barth et al., Chem. Abst. Vol. 42, 4679 i, describes the hemostyptic effect of protopectins. Lowery, Archives of Surgery, Vol. 60, p. 793–805, describes testing films of various materials including alcohol, sodium carboxymethylcellulose, sucrose, pectin, and various gums for their hemostatic properties.

Cyr et al. in U.S. Pat. No. 3,312,594 describe forming a dry blend of sodium carboxymethylcellulose, pectin, and gelatin and then compressing the powder into a tablet which can include a pharmaceutically active ingredient.

Chen in U.S. Pat. No. 3,339,546 is directed to an adhesive composition for use on moist body surfaces. the composition includes one or more water soluble or swellable hydrocolloids such as pectin, gelatin, and CMC and a viscous gum like substance such as natural rubber, silicone rubber, acrylonitrile rubber, polyurethane rubber, polyisobutylene, sucrose acetate isobutylate, etc. The viscous substance acts as a binder for the hydrocolloid particles and renders the final bonding composition elastic and pliable. These ingredients are combined by heating and mixing to form a dough-like substance which is then passed through a roller mill and then flattened in a hydraulic press. A layer of water impervious polymeric film material can then be pressed over one side of the flattened bonding mass as taught in Example 1.

Etes in U.S. Pat. No. 3,640,741 disclose an adhesive mass that is the reaction product of a hydrophilic colloid and a cross-linking agent in the presence of an organic liquid medium such as glycerin.

Lachman et al., Journal of the American Pharmaceutical Association, Vol. 46, p. 412–416, describe freeze drying various synthetic gums and suspending agents including gelatin, pectin and carboxymethylcellulose to increase their solubility.

Falb et al. in U.S. Pat. No. 3,438,374 describe a tissue bonding adhesive and hemostatic product of cross-linked gelatin or collagen and a phenol such as resorcinol.

SUMMARY OF THE INVENTION

This invention is directed to a medically useful lyophilized foam sponge product prepared from a mixture of gelatin, pectin, and sodium carboxymethylcellulose and having a density of from about 0.01 to about 0.10 grams/cc. The pectin and sodium carboxymethylcellulose are each present at from about 10% to about 50% by weight of the final product and the gelatin is present at from about 20% to about 80% by weight of the final product.

This invention is also directed to the method of preparing this lyophilized foam sponge product. This method includes dry blending the gelatin, pectin, and sodium carboxymethylcellulose, adding the mixture to water with agitation so as to form a colloidal dispersion having a solids content of from about 1% to about 20% by weight, foaming the colloidal dispersion so that its volume increases from about 10% to about 600%, freezing, and then freeze drying.

DETAILED DESCRIPTION

The product of this invention is a white spongy foam material whose characteristics vary somewhat depending upon the composition and processing techniques. The composition and method of preparation, which are explained in detail below, permit the product to be obtained in the form of a sheet which can be sliced or cut to a desired size or milled into a granular form. The product can also be cast into discrete shapes such as cones, tampons, suppositories, etc.

The lyophilized product of this invention is capable of absorbing and holding many times its weight of whole blood or body exudates. The product is also bioabsorbable. Thus, it can be employed as a hemostatic agent to control visceral bleeding in areas of the body such as the pancreas, liver, or kidney where conventional means of control are technically impractical. The product can also be employed as an absorbable sponge in surgical procedures and for supportive surgical uses. The product can also be employed in the treatment of various open wounds such as decubitus and varicose ulcers.

The lyophilized foam product because of its hydrocolloid composition possesses wet-tack. Thus, the product can be employed as a bioabsorbable tissue adhesive for surgical procedures involving non-suturable tissue and in burn treatment and also as an adhesive in skin grafting procedures.

The solubility and absorbability of the lyophilized foam product can be reduced by crosslinking either before or after the lyophilization step. For some medical uses it may be preferable to have a partially insoluble product, for example in the adhesion of tissues, and in other medical uses a practically insoluble product may be preferred, for example when the product is shaped to be used as a colostomy plug.

As a result of the unique combination of hemostatic, adhesive, bioabsorbability, and physical characteristics of the lyophilized foam product of this invention, it can be employed in numerous medicinal and veterinary procedures.

The lyophilized foam sponge product of this invention is formed from a mixture of gelatin, pectin, and sodium carboxymethylcellulose. The pectin and sodium carboxymethylcellulose are each present at from about 10% to about 50% by weight of the final product and the gelatin is present at from about 20% to about 80% by weight of the final product. In general, as the amount of gelatin is increased the final product becomes more pliable. The foam sponge product will have a density of from about 0.01 to about 0.1 grams/cc.

Preferably the pectin and sodium carboxymethylcellulose will each be present at from about 15% to about 35% by weight of the final product and the gelatin will be present at from about 30% to about 70% by weight of the final product.

The foam sponge product of this invention is prepared by first forming a dry blend of gelatin, pectin, and sodium carboxymethylcellulose. Preferably, these materials are comminuted to a finely divided form so as to aid in their mixing and increase the rate at which they will hydrate. Of course, these materials as well as any of the other materials described below that may be employed in this invention should be of a pharmaceutically acceptable purity. The dry blend is then added with agitation to water to form a colloidal dispersion. Any conventional mixing device having a propeller, gate mixer, or homomixer can be employed. The amount of water and dry blend are controlled so that the initial dispersion has a solids content of from about 1% to about 20% by weight. The density and toughness of the final product will vary depending upon the solids content and the degree of aeration or foaming. Thus, the product obtained from a colloidal dispersion having a solids content of about 1% by weight will be relatively fluffy and soft whereas a product obtained from a colloidal dispersion having a solids content of about 5% or greater aerated or foamed to the same extent will be more rigid and tough. Preferably, the colloidal dispersion contains from about 3% to about 9% by weight of the dry blend of gelatin, pectin, and sodium carboxymethylcellulose and will result in a final product having a density of from about 0.01 to about 0.03 grams/cc. depending upon the degree of aeration or foaming.

In order to obtain a uniform product, the aqueous colloidal dispersion is aerated or foamed prior to freezing. The aeration or foaming increases the volume of the dispersion to about 10% to about 600% of the original volume. The presence of gas bubbles such as air or carbon dioxide prevents or at least retards depending upon the extent of entrainment the formation of patterns in the lyophilized final product. Patterns are the result of ice crystal lattices forming in the dispersion during the freezing step and if present in the final product they are a source of nonuniformity and can cause mechanical weakness. Gas entrainment can be performed by whipping the dispersion and/or by means of a tube having a fitted cylinder that injects air or other gas into the dispersion. Dry ice can be used to generate carbon dioxide in the dispersion. Before freezing the aerated or foamed colloidal dispersion should contain from approximately 10% to about 85% by volume of entrapped gas, preferably about 60% by volume.

The foamed or aerated aqueous colloidal dispersion can be prepared at room temperature. Elevated temperatures could be employed to ensure dispersal of the hydrocolloids.

A surface tension modifier such as sodium hexametaphosphate or natural or synthetic surfactants such as lecithin and polyoxyethylene derivatives of sorbitan fatty acid esters such as Tween 60 can be added to the colloidal dispersion to stabilize the gas suspension and enhance the quality of the foam. Such agents can be added in varying amounts depending upon their surfactant ability but in general will vary from about 10% to about 100% by weight of the solids already present in the colloidal dispersion.

The foamed or aerated colloidal dispersion is then poured into metal or plastic containers and frozen. The rate of heat transfer is important since at low levels of gas entrainment, if the dispersion is frozen too slowly, the gas bubbles may rise to the surface causing nonuniformity. In order to minimize variations in the freezing step, it is preferred that small containers be employed and that freezing step be performed in a well circulated cold room that is kept at about −20° C. The frozen material is then lyophilized in a conventional freeze drying apparatus at less than about 20° C. and a vacuum of about 50 to 150 microns of Hg. After drying has been completed, the foam sponge product is maintained in a dry atmosphere (relative humidity less than 50%) to prevent condensation of moisture. The foam sponge product can then be cut into the desired size, shape and thickness and hermetically sealed in a plastic bag or glass container. The packaged product can be terminally sterilized by gamma radiation of about 1.5 mega rad.

Of course, if desired, the foamed aqueous colloidal dispersion can be freeze dried in a mold tray so to obtain the final product having a particular shape. Alternatively, a granular final product can be obtained by passing the dried foam sponge product through a screen before packaging. Preferably, a number 16 mesh screen is employed so as to obtain a granular product having a particle size of less than one mm.

The lyophilized hydrocolloid foam product can be cross-linked so as to reduce its solubility and absorbability. For example, a solution of a cross-linking agent such as formaldehyde, glutaraldehyde, alum or tannin can be added to the aerated or foamed colloidal dispersion at from about 0.1% to about 10% by weight of the combined gelatin, pectin, and sodium carboxymethylcellulose. Alternatatively, the product can be cross-linked after the lyophilization step by exposing the freeze dried product to formaldehyde or glutaraldehyde vapor or ultraviolet radiation. As the amount of cross-linking increases the solubility of the product decreases.

Various pharmaceutically active compounds such as antimicrobial agents can also be added to aerated or foamed colloidal dispersion. In particular, where the product is intended for use as a hemostatic agent or surgical sponge, thrombin or other hemostatically useful substances can be added directly to the aerated or foamed colloidal dispersion.

Other substances can also be added to the aerated or foamed colloidal suspension. Plasticizers such as propylene glycol or glycerine can be included within the colloidal dispersion at up to about 30% by weight of the combined gelatin, pectin, and sodium carboxymethylcellulose. The addition of a plasticizing agent will enhance the flexibility and strength of the final product.

As discussed above, the foam sponge products of this invention have a density of from about 0.01 to 0.10 gm./cc. depending upon the weight percent of gelatin, pectin, and sodium carboxymethylcellulose. The foam sponge products of this invention can absorb from about 350% to about 900% of their own weight of heparinized whole blood and from about 700% to about 1500% of their own weight of water.

The water absorption rate of the foam sponge products of this invention are tested by placing a 0.75 inch by 0.75 inch piece on a sintered glass filter attached with a graduate pipet. The time required to have 0.05 ml. of water absorbed is found to be from about 30 to 100 seconds for the foam sponge product in which no cross-linking agent is present and from about 100 to 150 seconds for the cross-linked foam sponge product.

The adhesive strength of the foam sponge products of this invention are tested by sandwiching a piece of the product between two strips of pre-soaked dialyzer tubing, 0.875 inch wide and two inches long, loaded with a 50 gm. weight for three minutes. These two strips adhered by the foam sponge product are pulled apart by Chatillon guage and a 1.2 cm./min. the break point is registered. According to this procedure the break point on the Chatillon gauge is from about 400 to 900 gms.

The following examples are illustrative of the invention.

EXAMPLE 1

A dry blend is formed consisting of 5 g. of sodium carboxymethylcellulose (extra fine), 5 g. of gelatin (Type A, high bloom, U.S.P. 100 mesh) and 5 g. of pectin (200 mesh). The mixture is passed twice through an 80 mesh screen. This dry blend is then slowly added to 500 ml. of water with vigorous agitation and a stream of air is blown into the bottom of the dispersion through a capillary tube. After approximately one hour, the colloidal dispersion becomes milky white and its volume increases to about 650 ml. The foamed dispersion is then poured into a 30 cm. by 45 cm. flat bottom metal tray and is frozen in a −20° C. cold room. After the dispersion is frozen solid the tray is transferred to a lyophilizer and the material is dried at −5° C. and 150 microns of Hg. After about 48 hours, the material is totally dried and it is removed from the lyophilizer and sliced to the desired size. The foam sponge product is then hermetically sealed inside a plastic bag or glass container and sterilized by gamma radiation at 1.5 Mrads.

This foam sponge product has a density of 0.04 gm/cc. and a pH of 4.5±0.3 which is determined by dissolving 0.1 g. in 10 ml. of water.

EXAMPLE 2

Sixty grams of a dry powder consisting of 30 g. of gelatin (Type B, low bloom, USP 100 mesh), 15 g. of sodium carboxymethylcellulose (fine) and 15 g. of citrus pectin (200 mesh) is rapidly added to 1 liter of purified water with vigorous agitation such as that produced by a ballon whip. Whipping is continued for approximately 10–15 minutes or until the volume of aerating foam is approximately 3 liters. The foam is then transferred to shallow pans (e.g., 45 cm.×45 cm.×1 cm.) or molds and is frozen at −5° to −20° C. for approximately six hours. The frozen material is then lyophilized at 50 to 100 microns for approximately 36 hours at 20° C. The density of the resulting flexible foam product is 0.02 gm/cc.

The material can be sliced into a desired size and hermetically packaged. If desired, the product can be sterilized by exposure to gamma radiation at 1.5 Mrads.

EXAMPLE 3

Following the procedure of Example 2 but employing as the powder a mixture of 54 g. of gelatin (Type A, high bloom, fine mesh), 18 g. of sodium carboxymethyl cellulose (fine), and 18 g. of citrus pectin (200 mesh), a foam product that is less flexible than that of Example 2 is obtained. This product has a density of about 0.03 g/cc.

EXAMPLE 4

Following the procedure of Example 2 but employing as the powder a mixture of 45 g. of gelatin (Type A, low bloom, fine mesh), 22.5 g. of sodium carboxymethylcellulose (fine), and 22.5 g. of citrus pectin (200 mesh), a foam product intermediate in flexibility to those of Examples 2 and 3 is obtained. This product has a density of about 0.03 g/cc.

EXAMPLES 5–20

Following the procedure of Example 1 or 2 but varying the materials as set forth below additional foam sponge products within the scope of the invention are obtained.

| Ex. | DRY BLEND Weight % Gelatin | Weight % Pectin | Weight % Na CMC | Weight % of Dry Blend In the Aq. Dis. | Volume % of Gas In the Aq. Dis. | Weight % Plasticizer (glycerol) Relative to Dry Blend in Aq. Dis. |
|---|---|---|---|---|---|---|
| 5  | 60   | 20   | 20   | 6   | 65 | — |
| 6  | 50   | 25   | 25   | 6   | 65 | 15 |
| 7  | 80   | 10   | 10   | 6   | 65 | — |
| 8  | 70   | 15   | 15   | 9   | 50 | — |
| 9  | 60   | 25   | 15   | 8   | 60 | — |
| 10 | 60   | 15   | 25   | 8   | 65 | — |
| 11 | 50   | 30   | 20   | 9   | 65 | — |
| 12 | 50   | 20   | 30   | 9   | 65 | — |
| 13 | 50   | 20   | 30   | 6   | 65 | — |
| 14 | 30   | 30   | 40   | 3   | 35 | — |
| 15 | 40   | 30   | 30   | 4   | 40 | — |
| 16 | 40   | 30   | 30   | 6   | 65 | — |
| 17 | 50   | 25   | 25   | 3   | 85 | — |
| 18 | 33.3 | 33.3 | 33.4 | 4.5 | 65 | 30 |
| 19 | 45   | 30   | 25   | 7   | 65 | — |
| 20 | 66   | 17   | 17   | 9   | 65 | — |

EXAMPLE 21

Following the procedure of Example 3 but adding from about 1 to about 5 ml. of formalin solution (37% by weight of formaldehyde gas in water) to the aerating foam prior to freezing and lyophilizing results in a foam that is almost completely insoluble in water.

Similarly, the aerating foams of Examples 1, 2 and 4 to 20 can be treated with formaldehyde prior to freezing and lyophilizing so as to cross-link one or more of the hydrocolloids and decrease the solubility of the final product.

Alternatively, the products of Examples 1 to 20 can be cross-linked after lyophilization by placing the product in a closed vessel for about two hours on a porous platform above a reservoir containing formalin solution. The formalin is presaturated with calcium chloride to maintain relative humidity at about 30 to 35%

EXAMPLE 22

Lyophilized thrombin is dispersed in a small volume of water at a concentration of approximately 10,000 units per 30 ml. This thrombin dispersion is added to the aerating foam of Example 1 and gently mixed. The thrombin containing foam is immediately frozen and then lyophilized according to the procedure of Example 1.

EXAMPLE 23

The following in vivo study was performed to evaluate the hemostatic and bioabsorbability of a sponge product of this invention as compared with the commercially available product Gelfoam ® (Upjohn).

Twelve New Zealand White rabbits weighing approximately 2.5 kg. and having ear tags for identification were used in the study. Each rabbit was anesthetized by intravenous injection of sodium pentobarbitol. The abdominal cavity was opened and the liver was exposed. An approximately 3 cm. thick slice of a lobe was incised, removed from the liver, and weighed. Immediately after incision, a piece of the sponge product prepared according to the procedure of Example 1 or Gelfoam was placed on the incisions of four rabbits each. Incisions of four additional rabbits were left uncovered to serve as control. The incision sites were observed for hemorrhage, and the blood loss from each animal was weighed upon clotting.

Upon cessation of bleeding, the test materials were left in place, the abdominal wall sutured, and the animals observed for survival. After ten days, all animals were necropsied, and the incision sites were examined for fate of the foam and any gross signs of tissue reaction. Mean blood loss from the group treated with the sponge product of Example 1 was compared to those of control and Gelfoam treated groups by Student's t test. Sections of liver at the incision sites were examined for histological changes.

Table 1 shows the individual weights of the blood loss and the slice of liver removed from each animal as well as their group mean values.

Incisions produced seepage of blood from the livers. The amount of blood loss was variable in the control and Gelfoam treated groups. Mean values of the blood loss were $6.10 \pm 1.76$ g. in the control, $6.08 \pm 2.06$ g. in the Gelfoam treated, and $0.97 \pm 0.2$ g. in the group treated with the product of Example 1. The difference between the control or Gelfoam groups and the group treated with the product of Example 1 was significant ($P < 0.05$).

TABLE I

| Group Number | Rabbit Number | Blood Loss (g.) | Liver Removed (g.) |
|---|---|---|---|
| I | 13 | 1.3 | 5.2 |
|   | 14 | 1.0 | 4.3 |
|   | 9  | 1.2 | 4.7 |
|   | 16 | 0.4 | 5.1 |
| Sponge Product of Example I | x̄ | 0.97 ±0.20 | 4.82 ±0.21 |
|   | I vs. III | p < .05 | not significant |
|   | I vs. II  | p < .05 | p < .01 |
| II | 17 | 4.3 | 7.2 |
|    | 18 | 2.6 (Blood collection incomplete) | 5.9 |
| Gelfoam | 19 | 5.4 | 5.9 |
|         | 20 | 12.0 | 6.5 |
|         | x̄ | 6.08 ∓2.06 | 6.38 ±0.31 |
|         | II or III | not significant | not significant |
| III | 5  | 10.6 | 4.0 |
|     | 11 | 2.7  | 4.8 |
|     | 1  | 7.1  | 7.3 |
|     | 7  | 4.0  | 7.1 |
| Control | x̄ | 6.10 | 5.80 |

TABLE I-continued

| Group Number | Rabbit Number | Blood Loss (g.) | Liver Removed (g.) |
|---|---|---|---|
|  |  | ±1.76 | ±0.83 |

Table II presents the results of pathological evaluation of incision sites in the liver of each animal. No test or control animal died during the ten day observation period.

On necrospsy, none of the sponge product from Example 1 was observed in the peritoneal cavity of any rabbit. Absence of this material was further confirmed on histological examination of the healed hepatic incisions. In animals treated with Gelfoam, however, the test material was still intact, grossly clearly distinguishable from the liver tissue, and adhered to the incision sites. Microscopically, it could be seen as a pink (hematoxylin-eosin-stained proteinaceous material) sponge infiltrated with blood of exudate. Gelfoam, therefore, was not absorbed during the 10-day period.

Livers of all animals were found to have healed with the formation of a scar at the incision sites. Histological evaluation of the incision sites revealed proliferation of fibroblasts, formation of giant cells indicating early hepatic regeneration, and focal necrosis or suppurative inflammation in some cases. Hepatic incision sites in three of the control animals showed hermorrhages. No hemorrhages were seen in either of the treated groups. Healing of the hepatic incisions in the three groups was similar, and no tissue reaction ascribable to the test materials was observed in any animal.

Thus, under the conditions of this study, the product of Example 1 was found to have a greater hemostatic effect than Gelfoam, was completely absorbed within 10 days, and elicited no tussue reaction in the peritoneal cavity.

TABLE II

| Group No./ Animal No. |  | Test Material | Scar | Suppa-ration | Giant Cells | Focal Necrosis | Focal Hemorrhage |
|---|---|---|---|---|---|---|---|
| Sponge Product of Example 1 |  |  |  |  |  |  |  |
|  | 9 | − | + | − | + | − | − |
|  | 13 | − | + | − | + | − | − |
| I | 14 | − | + | − | + | − | − |
|  | 16 | − | + | + | + | + | − |
| Gelfoam |  |  |  |  |  |  |  |
|  | 17 | + | + | − | + | − | − |
|  | 18 | + | + | − | + | + | − |
| II | 19 | + | + | − | + | − | − |
|  | 20 | + | + | + | + | − | − |
| Control |  |  |  |  |  |  |  |
|  | 1 | − | + | − | + | − | − |
|  | 5 | − | + | − | + | + | + |
| III | 7 | − | + | − | + | − | + |
|  | 11 | − | + | − | + | + | + |

− = absent
+ = present

What is claimed is:

1. A medically useful lyophilized sponge product having a density of from about 0.01 to about 0.10 gm/cc, said sponge product comprising a mixture of the hydrocolloids, gelatin, pectin, and sodium carboxymethylcellulose, said pectin and sodium carboxymethylcellulose each being at from about 10% to about 50% by weight of the final product and said gelatin being present at from about 20% to about 80% by weight of the final product.

2. The product of claim 1 wherein said pectin and sodium carboxymethylcellulose are each present at from about 15% to about 35% by weight of the final product and said gelatin is present at from about 30% to about 70% by weight of the final product.

3. The product of claim 2 wherein said gelatin, pectin, and sodium carboxymethylcellulose are present in about the same amount by weight.

4. The product of claim 3 having a density of about 0.04 gm/cc.

5. The product of claim 2 wherein said gelatin is present at about 50% by weight and said pectin and sodium carboxymethylcellulose are each present at about 25% by weight.

6. The product of claim 5 having a density of about 0.02 gm/cc.

7. The product of claim 5 having a density of about 0.03 gm/cc.

8. The product of claim 2 wherein said gelatin is present at about 60% by weight and said pectin and sodium carboxymethylcellulose are each present at about 20% by weight.

9. The product of claim 8 having a density of about 0.03 gm/cc.

10. The product of claim 1 wherein one or more of said hydrocolloids is cross-linked.

11. The product of claim 1 wherein a pharmaceutically active material is included within the sponge.

12. The product of claim 11 wherein the pharmaceutically active material is thrombin.

13. The product of claim 1 having enhanced flexibility resulting from the inclusion of a plasticizer.

14. The process of providing hemostatis at the site of a wound which comprises contacting the wound with an effective amount of the foam sponge product of claim 1.

15. The process of adhering bodily tissue which comprises pressing an effective amount of the foam sponge product of claim 1 between the sections of tissue.

16. A process for preparing a medically useful sponge product comprising
(a) forming a dry blend comprising a mixture of the hydrocolloids, gelatin, pectin, and sodium carboxymethylcellulose said pectin and sodium carboxymethyl cellulose each being present at from about 10% to about 50% by weight of product and said gelatin being present at from about 20% to about 80% by weight of the product;
(b) adding said dry blend to water with agitation to form a colloidal dispersion said dispersion having a solids content of from about 1% to about 20% by weight;
(c) aerating or foaming the colloidal dispersion so that its volume increases by about 10% to about 600%;
(d) pouring said aerating or foaming dispersion into a suitable receptacle;
(e) freezing; and
(f) lyophilizing.

17. The process of claim 16 wherein said pectin and sodium carboxymethylcellulose are each present at from about 15% to about 35% by weight of the final product and said gelatin is present at from about 30% to about 70% by weight of the final product; and wherein said colloidal dispersion contains from about 3% to about 9% by weight of the blend of pectin, gelatin, and sodium carboxymethylcellulose.

18. The process of claim 17 wherein said gelatin, pectin, and sodium carboxymethylcellulose are present in the dry blend in about the same amount by weight.

19. The process of claim 18 wherein said dispersion contains about 3% by weight of said dry blend and said foaming step is performed by blowing a stream of air to the bottom of said dispersion so as to expand its volume by about 30%.

20. The process of claim 17 wherein said gelatin is present at about 50% by weight and said pectin and sodium carboxymethylcellulose are each present at about 25% by weight in the dry blend.

21. The process of claim 20 wherein said colloidal dispersion contains about 6% by weight of said dry blend and wherein the aeration of the colloidal dispersion increases its volume by about 65%.

22. The process of claim 20 wherein said colloidal dispersion contains about 9% by weight of said dry blend and wherein the aeration of the colloidal dispersion increases its volume by about 65%.

23. The process of claim 17 wherein said gelatin is present at about 60% by weight and said pectin and sodium carboxymethylcellulose are each present at 20% by weight in the dry blend.

24. The process of claim 23 wherein said colloidal dispersion contains about 9% by weight of said dry blend and wherein the aeration of the colloidal dispersion increases its volume about 65%.

25. The process of claim 16 wherein a cross-linking agent is added to the colloidal dispersion at from about 0.1% to about 10% by weight based upon the weight of dry blend in the dispersion.

26. The process of claim 16 wherein the lyophilized product is exposed to a vaporized cross-linking agent.

27. The process of claim 16 wherein a pharmaceutically active material is added to the colloidal dispersion.

28. The process of claim 27 wherein the pharmaceutically active material is thrombin.

29. The process of claim 16 wherein a plasticizing agent is added to the colloidal dispersion at up to about 30% by weight based upon the weight dry blend in the solution.

30. The process of claim 16 wherein a surfactant is added to the colloidal dispersion to stabilize and enhance the quality of the foam.

* * * * *